United States Patent [19]

Mebes

[11] Patent Number: 5,000,918
[45] Date of Patent: Mar. 19, 1991

[54] METHOD OF DISINFECTING PETROLEUM AND PETROLEUM PRODUCTS

[75] Inventor: Bruno Mebes, Burgdorf, Switzerland

[73] Assignee: Sanitized Verwertungs A.-G., Luzern, Switzerland

[21] Appl. No.: 90,460

[22] Filed: Aug. 28, 1987

Related U.S. Application Data

[63] Continuation of Ser. No. 803,621, Dec. 2, 1985, abandoned.

[30] Foreign Application Priority Data

Dec. 10, 1984 [CH] Switzerland ................. 5852/84

[51] Int. Cl.$^5$ .................. A61L 2/18; C02F 1/68
[52] U.S. Cl. ...................... 422/34; 210/764
[58] Field of Search ............... 422/34; 210/764

[56] References Cited

U.S. PATENT DOCUMENTS

| | | | |
|---|---|---|---|
| 2,680,058 | 6/1954 | Harris et al. | 210/764 X |
| 3,169,906 | 2/1965 | Donchak et al. | 422/34 X |
| 3,256,143 | 6/1966 | Zedler | 210/764 X |
| 3,624,213 | 11/1971 | Cherkas | 422/34 X |
| 4,200,633 | 4/1980 | Quinlan | 210/764 X |
| 4,200,634 | 4/1980 | Quinlan | 210/764 X |
| 4,518,610 | 5/1985 | Umekawa et al. | 210/764 X |
| 4,552,752 | 11/1985 | Amick | 210/764 X |

FOREIGN PATENT DOCUMENTS

| | | | |
|---|---|---|---|
| 19470 | 11/1980 | European Pat. Off. | |
| 79308 | 5/1983 | European Pat. Off. | 210/764 |

OTHER PUBLICATIONS

Naylon et al., *Chemical Abstracts*, 70 (22), #1054265.
Lopes et al., *Chemical Abstracts*, 86 (11), #70669z.
Ruseska et al., Oil & Gas Journal, Mar 8, 1982, "Biocide Testing Against Corrosion-Causing Oil-Field Bacteria Helps Control Plugging."

*Primary Examiner*—Robert J. Warden
*Assistant Examiner*—Jill Johnston
*Attorney, Agent, or Firm*—Zarley, McKee, Thomte, Voorhees & Sease

[57] ABSTRACT

The method uses propylene oxide as the active substance. It is particularly suitable for inhibiting undesirable growth of microorganisms in drilling for petroleum.

8 Claims, No Drawings

METHOD OF DISINFECTING PETROLEUM AND PETROLEUM PRODUCTS

This is a continuation of U.S. patent application Ser. No. 803,621 filed on Dec. 2, 1985, now abandoned.

This invention relates to methods of disinfection, and more particularly to a method of disinfecting petroleum and petroleum products, especially for inhibiting the growth of microorganisms capable of living therein. The method is well suited for application in drilling for petroleum.

In exploring for petroleum, as well as in its processing, the individual operations may be disturbed by microbial contamination. The growth of microorganisms in oils requires the presence of water, a source of nitrogen, and necessary trace elements. These growth prerequisites are met in most of the oil fields now being exploited. For example, in the case of offshore recovery, undesirable microorganisms are transferred to the oil well through drilling and also through the injection of large quantities of sea water. These microorganisms, or their metabolites, can lead to trouble in conveyance of the oil, e.g., plugging of pipelines, gas formation, or corrosion of installations.

For inhibiting the growth of such microorganisms, biocides such as glutaraldehyde, acrolein, or quaternary ammonium compounds (quats) are used. However, these disinfectants exhibit certain drawbacks, such as substantivity to the surface or resinification. Suitable biocides for use in oilwell drilling must be ecologically inoffensive, cover a broad microbial spectrum, be effective in low concentrations, not act selectively, and have adequate stability at the temperatures of use. Furthermore, the biocides should not cause any corrosion, and they should be easy to handle and inexpensive. The prior art agents can lead to undesirable flow losses, to sedimentation, and even to blockages, constituting serious distrubances of operations.

It is an object of this invention to provide an improved method of disinfecting petroleum and petroleum products whereby the microorganisms can be effectively combated without the aforementioned drawbacks.

To this end, in the method according to the present invention, a microbiocidal amount of propylene oxide is added to the crude oil or to the petroleum products.

In this method of disinfection, the propylene oxide is generally mixed with an inert carrier in a suitable concentration, so that safe handling of the agent is ensured.

Owing to their compatibility with the chemicals used in the petroleum industry and with the petroleum itself, propylene oxide and the preferred carrier materials can be quantitatively regulated and applied satisfactorily in all stages of processing.

The disinfecting method according to this invention can be applied not only in drilling for oil but also in further process stages and in the storage of petroleum products. The presence of water, in particular, makes petroleum and petroleum products susceptible to microorganisms. The method is therefore especially suitable for petroleum and petroleum products with which water is also present. Thus it is possible, for example, to convey the propylene oxide into the oil well by means of the water at the time of completion. Microorganisms in the water are thereby already combated during such conveyance and cannot contaminate the oil if a minimum concentration of propylene oxide is maintained. Through the contact between the petroleum and the water containing the propylene oxide, part of the propylene oxide passes into the petroleum, where it can likewise develop its biocidal activity.

The propylene oxide is preferably applied in a quantity such that the system to be disinfected exhibits a propylene oxide concentration of 15-20 ppm. Suitable carrier materials for such application are light kerosene, polyether compounds such as nonylphenol polyglycol ether having 10 units of ethylene oxide or fatty alcohol polyglycol ether having 12-16 carbons in the alcohol portion and 10-12 units of ethylene oxide, water, or mixtures thereof. In addition, anion-active, cation-active, and amphoteric emulsion systems are also suitable.

The following examples represent preferred embodiments of formulations of propylene oxide as may be utilized in the method of the present invention.

EXAMPLE 1

A mixture of the following components is prepared:
15 parts by weight of propylene oxide,
50 parts by weight of light kerosene, and
35 parts by weight of nonylphenol polyglycol ether having 10 units of ethylene oxide.

This mixture is suitable for use in water-in-oil or oil-in-water systems. Effective disinfection of the systems is achieved when the propylene oxide concentration is 5-20 ppm.

EXAMPLE 2

The following components are mixed:
20 parts by weight of propylene oxide,
40 parts by weight of white spirit, and
40 parts by weight of fatty alcohol polyglycol ether having 12-16 carbons in the alcohol portion and 10-12 units of ethylene oxide.

For disinfecting a mixture of oil and water, this formulation is added in a concentration such that a propylene oxide concentration of 5-20 ppm results.

The mixture obtained is put into a pressure-metering pump system in the pipe system to be treated. The rate of flow is adjusted so that the concentration of propylene oxide in the system to be disinfected is at least 5-20 ppm. This results in excellent disinfection. ethylene oxide can likewise be used as the disinfectant in the same way and with the same effect. Owing to its physical properties, however, this substance has disadvantages in handling as compared with propylene oxide.

The following table illustrates the method of disinfection according to the invention as applied to an oil emulsion contaminated with microorganisms. Similar contaminated oil emulsions treated with glutaraldehyde, on the one hand, and untreated contaminated oil emulsions, on the other hand, are used for purposes of comparison.

TABLE I

Effect of Proplyene Oxide on Various Problem Bacteria in the Petroleum Industry as Compared with Glutataldehyde Test conditions: number of bacteria per ml of oil emulsion = log 5
oil emulsion: 15% crude oil, 75% water with emulsifier
contact time: 15 and 30 min., respectively
disinfectant: 20 ppm of glutaraldehyde and 20 ppm of propylene oxide, respectively
temperature: 25° C.

| | Contact Time in Min. | | | | |
|---|---|---|---|---|---|
| | 15 min. | | 30 min. | | |
| Type of Bacteria | without | with | without | with | Disinfectant/Application |
| Pseudomonas aeruginosa ATCC 15442 | + + + + | − − − − | + + + + | − − − − | Formulation and application according to Example 1 |
| Pseudomonas aeruginosa ATCC 15442 | + + + + | +(+) | + + + + | + | Glutaraldehyde |
| E. coli ATCC 11229 | + + + + | (+)(+) | + + + + | − − − − | Formulation and application according to Example 1 |
| E. coli ATCC 11229 | + + + + | + + | + + + + | (+)(+) | Glutaraldehyde |
| Proteus vulgaris ATCC 6896 | + + + + | + | + + + + | − − − − | Formulation and application according to Example 1 |
| Proteus vulgaris ATCC 6896 | + + + + | + + | + + + + | (+)(+) | Glutaraldehyde |
| Staph. aureus ATCC 6538 | + + + + | − − − − | + + + + | − − − − | Formulation and application |
| Staph. aureus ATCC 6538 | + + + + | (+) | + + + + | − − − − | Glutaraldehyde |
| Bact. subtilis ATCC 6633 | + + + + | + | + + + + | − − − − | Formulation and application according to Example 1 |
| Desulfovibrio salexigenes ATCC 14822 NCIB 8403 | + + + + | − − − − | + + + + | − − − − | Formulation and application according to Example 1 |
| Desulfovibrio salexigenes ATCC 14822 NCIB 8403 | + + + + | + + + | + + + + | + + | Glutaraladehyde |
| Sphaerotilus natans | + + + + | − − − − | + + + + | − − − − | Formulation and application according to Example 2 |
| Sphaerotilus natans | + + + + | + + | + + + + | + | Glutaraldehyde |
| Saccharomyces cerevisiae | + + + + | + + | + + + + | − − − − | Formulation and application according to Example 2 |
| Saccharomyces cerevisiae | + + + + | + + | + + + + | + | Glutaraldehyde |
| Aspergillus niger ATCC 6275 | + + + + | (+) | + + + + | − − − − | Formulation and application according to Example 2 |
| Aspergillus niger ATCC 6575 | + + + + | + + + | + + + + | + + | Glutaraldehyde |
| Penicillium funiculosum IAM 7013 | + + + + | − − − − | + + + + | − − − − | Formulation and application according to Example 2 |
| Penicillium funiculosum IAM 7013 | + + + + | + | + + + + | − − − − | Glutaraldehyde |

Legend:
+ + + + = uninhibited growth
+ + + = app. 25% inhibition of growth
+ + = app. 50% inhibition of growth
+ = app. 75% inhibition of growth
(+) = very weak growth
− = no growth The biocide utilized in the present invention as compared with prior art biocides utilized in drilling for petroleum.

The following biocides are used for disinfecting water-circulation systems in drilling for petroleum (e.g., drilling fluids). At the present time, only a limited number of chemicals are employed in the field of petroleum recovery and processing.

| Biocide | Concentration in ppm |
|---|---|
| Isothiazoline | 15–30 |
| Glutaraldehyde | 25–100 |
| Aliphatic amines | 50–110 |
| Quaternary ammonium compounds | 50–100 |
| Acrolein | 5–15 |
| Dibromonitrilopropionamide | 30–80 |
| Propylene oxide (according to the present invention) | 5–10 |

In an article entitled, "Biocide testing against corrosion-causing oil-field bacteria helps control plugging," by I. Ruseska et al., published in the Mar. 8, 1982, edition of Oil & Gas Journal, it was demonstrated that suitable active biocides must be capable of penetrating biofilms in order to destroy microorganisms. The pipes are generally covered by the "glycocalyx," an anionic polysacccharide matrix, and the microorganisms are embedded in this matrix. This means that the active biocidal component must be soluble in polar and apolar systems. An active substance which is soluble only in water influences only the rate of growth of non-sessile bacteria but has no effect in combating sessile bacteria such as sulfate-reducing bacteria (SRB type).

The results of a screening test are listed in the following Table II. The tests were carried out with a Robbins Device as described in an article entitled, "Observations on biofilm formation," by W. I. McCoy, et al., published in the Canadian Journal of Microbiology, Vol. 27, 1981, pp. 910–917.

TABLE II

Bacterial Growth under Aerobic and Anaerobic Conditions, Non-Stationary Phase cbu/sq. cm.* in log units

| Biocides Used in Test | ppm | Aerobic, sessile bacteria cbu/sq. cm. Pseudomonas aeruginosa ATCC 15442 | | | | Sulfate-reducing sessile bacteria | | | | Glycocalyx Film | | |
|---|---|---|---|---|---|---|---|---|---|---|---|---|
| | | | | | | cbu/sq. cm. | | SRB wild strain | | | | |
| | | 6 hrs | 12 hrs | 24 hrs | 48 hrs | 6 hrs | 24 hrs | 48 hrs | 72 hrs | 24 hrs | 48 hrs | 72 hrs |
| Glutaraldehyde 40% | 25 | log 8.4 | log 8.8 | log 7.2 | log 7.4 | log 8.2 | log 8.7 | log 8.2 | log 7.3 | + | + | ++ |
| Glutaraldehyde 40% | 50 | log 7.8 | log 5.7 | log 5.2 | log 4.8 | log 8.1 | log 7.4 | log 6.9 | log 5.1 | + | + | (+) |
| Glutaraldehyde 40% | 100 | log 6.8 | log 5.1 | log 4.6 | log 3.8 | log 7.2 | log 6.4 | log 4.9 | log 4.6 | − | − | − |
| Acrolein 98% | 2 | log 7.9 | log 6.8 | log 5.9 | log 4.7 | log 8.1 | log 7.2 | log 6.1 | log 5.1 | + | (+) | − |
| Acrolein 98% | 5 | log 6.6 | log 5.3 | log 4.6 | log 3.7 | log 7.7 | log 6.4 | log 5.0 | log 4.1 | + | − | − |
| Acrolein 98% | 10 | log 4.9 | log 3.6 | log 2.1 | < log 2 | log 4.8 | log 3.3 | log 2.3 | < log 2 | − | − | − |
| Propylene oxide in wh. spirit | 2 | log 7.3 | log 6.7 | log 5.8 | log 4.5 | log 7.9 | log 7.3 | log 5.9 | log 4.9 | + | − | − |
| Propylene oxide in wh. spirit | 5 | log 6.2 | < log 2 | < log 2 | < log 2 | log 5.9 | < log 2 | < log 2 | < log 2 | − | − | − |
| Propylene oxide in wh. spirit | 10 | < log 2 | < log 2 | < log 2 | < log 2 | log 3.1 | < log 2 | < log 2 | < log 2 | − | − | − |

*Colony-building units per sq. cm. = no. of bacteria per sq. cm.

What is claimed is:

1. A method of disinfecting a petroleum crude system, and the raw products obtained therefrom, without causing ecological harm, or undesirable flow losses, or other operational disturbances in petroleum extraction operations, said method comprising:
   adding to the petroleum crude a small but microbiocidally effective amount of propylene oxide to provide a propylene oxide level in the crude system of from about 5 ppm to about 20 ppm to inhibit growth of undesirable microorganisms.

2. The method of claim 1 wherein the propylene oxide is added with an inert carrier.

3. The method of claim 2 wherein the inert carrier contains a mixture of light kerosene and nonyl phenyl polyglycol ether having 10 molar equivalents of ethylene oxide.

4. The method of claim 2 wherein the inert carrier contains a mixture of white spirit terpentine substitute, representing a petroleum fraction comprising certain high-boiling types of gasoline, and $C_{12-16}$ fatty alcohol polyglycol ether having 10–12 molar equivalents of ethylene oxide.

5. The method of claim 2 wherein the inert carrier is selected from the grup consisting of anion-active, cation-active, and amphoteric emulsion systems.

6. The method of claim 1, wherein the concentration of propylene oxide in the petroleum and petroleum product is from about 15 to about 20 ppm.

7. A method of claim 1 used in petroleum recovery by means of water injection, the improvement comprising the step of adding the propylene oxide mixture to the injected water.

8. A method of disinfecting petroleum crude comprising: adding propylene oxide to water to create a solution
   concentrate of propylene oxide in water; and therafter injecting the water solution concentrate of propylene oxide
   into the petroleum crude product to provide a petroleum product having a propylene oxide concentration of from about 15 ppm to about 20 ppm of propylene oxide as a microbiocidally effective agent which prevents undesirable bacterial growth without causing any ecological harm or undesirable flow losses during crude oil operational processing.

* * * * *